US012612853B2

(12) United States Patent
Dave et al.

(10) Patent No.: US 12,612,853 B2
(45) Date of Patent: Apr. 28, 2026

(54) CEMENT HEALTH MONITORING IN CCUS WELLS

(71) Applicant: Halliburton Energy Services, Inc., Houston, TX (US)

(72) Inventors: Jalpan P. Dave, Singapore (SG); Paul J. Jones, Houston, TX (US); Dinesh Ananda Shetty, Houston, TX (US); Fraser Murray, Singapore (SG); David Yan Lap Wong, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 18/601,202

(22) Filed: Mar. 11, 2024

(65) Prior Publication Data

US 2025/0283402 A1    Sep. 11, 2025

(51) Int. Cl.
| | |
|---|---|
| *E21B 47/005* | (2012.01) |
| *E21B 34/06* | (2006.01) |
| *E21B 47/10* | (2012.01) |
| *E21B 49/08* | (2006.01) |
| *G01N 21/31* | (2006.01) |
| *G01N 33/28* | (2006.01) |
| *G01V 20/00* | (2024.01) |

(52) U.S. Cl.
CPC ............ *E21B 47/005* (2020.05); *E21B 49/08* (2013.01); *G01N 21/31* (2013.01); *G01N 33/2817* (2013.01); *G01V 20/00* (2024.01); *E21B 34/06* (2013.01); *E21B 47/10* (2013.01); *E21B 2200/20* (2020.05)

(58) Field of Classification Search
CPC ........ E21B 47/005; E21B 49/08; E21B 34/06; E21B 47/10; E21B 2200/20; G01N 21/31; G01N 33/2817; G01V 20/00
See application file for complete search history.

(56) References Cited

U.S. PATENT DOCUMENTS

| | | | |
|---|---|---|---|
| 8,547,556 | B2 | 10/2013 | Irani |
| 9,435,192 | B2 | 9/2016 | Lawrence et al. |
| 9,891,166 | B2 | 2/2018 | Wild et al. |
| 11,221,431 | B2 | 1/2022 | Fujisawa et al. |
| 2010/0257926 | A1* | 10/2010 | Yamate ................... E21B 49/00 73/152.23 |
| 2011/0042074 | A1 | 2/2011 | Goldberg |
| 2011/0192598 | A1 | 8/2011 | Roddy et al. |
| 2012/0081696 | A1 | 4/2012 | Boersma et al. |

(Continued)

FOREIGN PATENT DOCUMENTS

| | | |
|---|---|---|
| WO | 2011146068 | 11/2011 |
| WO | 2013089811 | 6/2013 |

OTHER PUBLICATIONS

"PCT Application No. PCT/US2024/020825 International Search Report and Written Opinion", Dec. 4, 2024, 13 pages.

*Primary Examiner* — James G Sayre
(74) *Attorney, Agent, or Firm* — DeLizio, Peacock, Lewin and Guerra, LLP

(57) ABSTRACT

Some implementations include a system comprising an electrical line positioned proximate to one or more subsurface formations; and a permanent downhole sensor array coupled to the electrical line, the permanent downhole sensor array including one or more downhole sensors, each downhole sensor including: a first sensing device configured to detect at least a first component of a downhole fluid.

20 Claims, 8 Drawing Sheets

(56) References Cited

U.S. PATENT DOCUMENTS

| | | |
|---|---|---|
| 2012/0206144 A1 | 8/2012 | Barlet-Gouedard et al. |
| 2017/0254191 A1* | 9/2017 | Barfoot .................... G01V 3/18 |
| 2021/0238979 A1 | 8/2021 | Stokely et al. |
| 2023/0112008 A1 | 4/2023 | Jandhyala et al. |

* cited by examiner

300

306

307

305

700

701 ∿ Processor

707 ∿ Memory

Bus

703 ∿

Network Interface ∿ 705

Reservoir Modeler ∿ 709

Device Controller ∿ 711

CEMENT HEALTH MONITORING IN CCUS WELLS

TECHNICAL FIELD

The disclosure generally relates to downhole tools for use in a wellbore formed in one or more subsurface formations, and in particular, completions tools for assessing cement integrity.

BACKGROUND

Carbon capture, utilization, and storage (CCUS) wells may be drilled and subsequently cemented for use in storing carbon dioxide ($CO_2$) in one or more subsurface formations. In CCUS wells, cement health degradation may be of particular concern. $CO_2$ may react with water to form carbonic acid. Carbonic acid may react with cement hydration products to yield calcium carbonate. These hydration products may further react to form the soluble bicarbonate species. Implications of the carbonation of cement may include reduced compressive strength, increased permeability, and a reduction in a well's operating lifetime. Monitoring cement health in CCUS wells may provide valuable information to an operator, a user, etc. who may in turn intervene and prevent the identified loss of cement integrity. Assessing and intervening in cement integrity issues before they become unmanageable may help extend the life of the CCUS well and improve asset value through proactive reservoir management.

Monitoring standards set by local government entities may also present a desire for permanent monitoring of CCUS storage reservoirs. During the $CO_2$ injection phase, an operator may be required to provide proof that their injection pressures are well below the formation fracture pressures, largely to avoid any potential channeling or fracturing into nearby formations or water tables. In some examples, the injection itself may last between two and twenty years, although other durations may be possible. Following $CO_2$ injection, the integrity of such containment zones may be monitored for a mandated amount of time. The mandated amount of time may span from ten years up to one hundred years. Therefore, a permanent monitoring system providing real-time data and a means for cement damage prevention, mitigation, etc. may extend the operating lifetime of the CCUS well.

BRIEF DESCRIPTION OF THE DRAWINGS

Implementations of the disclosure may be better understood by referencing the accompanying drawings.

FIGS. 1-8 and the operations described herein are examples meant to aid in understanding example implementations and should not be used to limit the potential implementations or limit the scope of the claims. None of the implementations described herein may be performed exclusively in the human mind nor exclusively using pencil and paper. None of the implementations described herein may be performed without computerized components such as those described herein. Some implementations may perform additional operations, fewer operations, operations in parallel or in a different order, and some operations differently.

DESCRIPTION OF SOME EXAMPLE IMPLEMENTATIONS

The description that follows includes example systems, methods, techniques, and program flows that embody implementations of the disclosure. However, it is understood that this disclosure may be practiced without these specific details. In other instances, well-known instruction instances, protocols, structures, and techniques have not been shown in detail in order not to obfuscate the description.

Overview

To assess cement integrity throughout the operating lifetime of a CCUS well, one or more downhole sensors each including a $CO_2$ sensing device may be communicatively linked to form a sensor array in a CCUS wellbore. Some implementations of the $CO_2$ sensing devices may include one or more micro-integrated computational element (ICE) sensors. This sensor array may be cemented in place in the well and may provide a user the ability to detect $CO_2$ throughout a length of the well for the operating lifetime of the well. The inlet of each downhole sensor may be protected with a filter that allows pore fluid to enter but prevents cement ingress from plugging and blocking the inlet. The readings from the one or more sensors forming the array may be used to improve a reservoir model. For example, the data from $CO_2$ ingress into the cement may provide information about the reservoir which may be used to train the reservoir model. The data may also be used to vary an injection profile of the CCUS well to protect cement health, thereby prolonging the operating life of the well. In some instances, collected data may even indicate that more $CO_2$ may safely be injected, further enhancing the value of the well.

Example Well System

Figure 1:
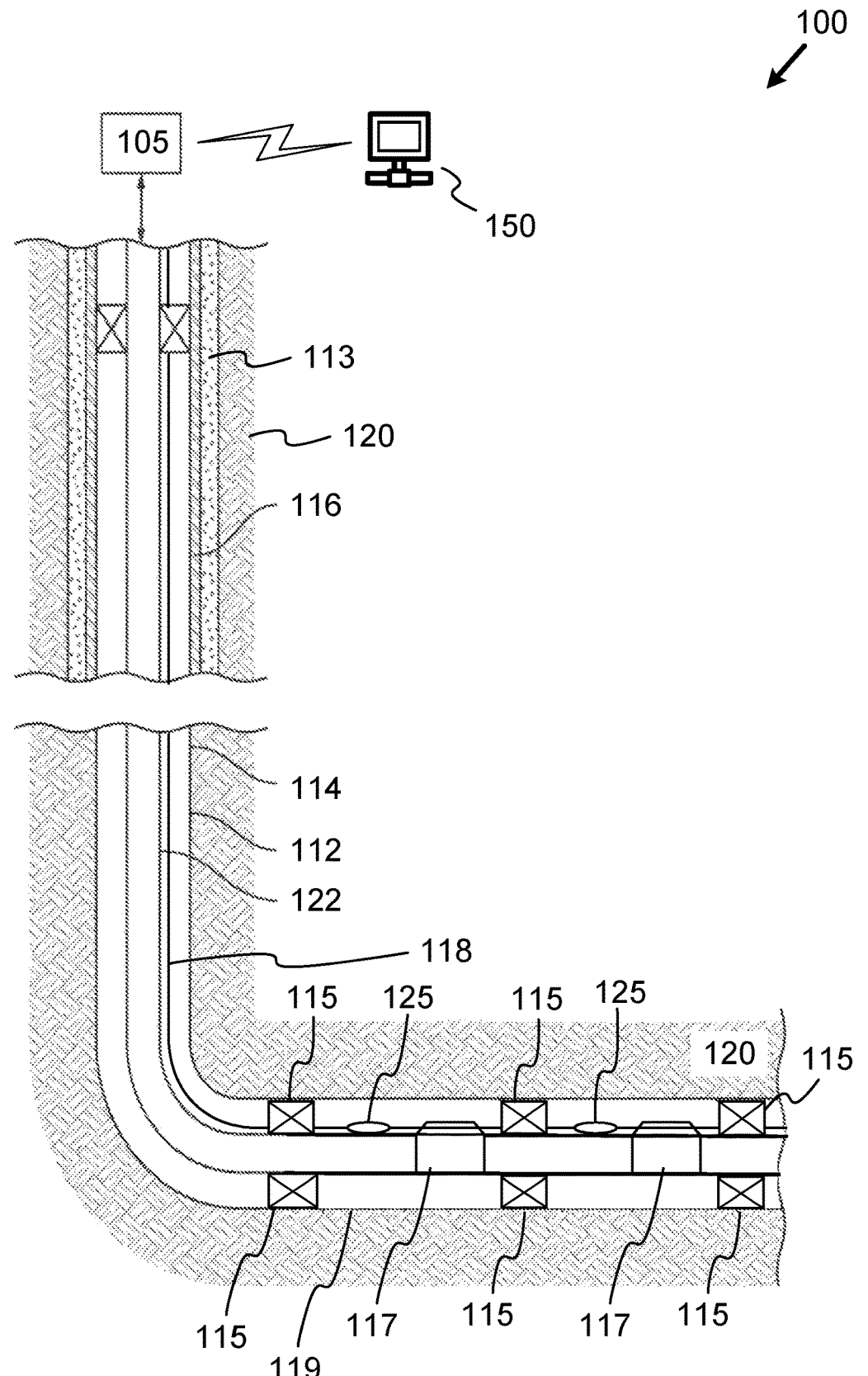
FIG. 1 is a cross-sectional diagram depicting an example well system including a sensor array, according to some implementations.

An example well system is now described. FIG. 1 is a cross-sectional diagram depicting an example well system including a sensor array, according to some implementations. A well system 100 may comprise a wellbore 112 which intersects a subsurface formation 120. The wellbore 112 may include a vertical section 114 and a horizontal section 119. However, other wellbore configurations may also be suitable. For example, some implementations may include the wellbore 112 as part of a vertical well.

Positioned within the wellbore 112 and extending from the surface is a tubing string 122 which provides a conduit for formation fluids to travel from the subsurface formation 120 to the surface and for fluids to travel from the surface to the subsurface formation 120. For example, supercritical $CO_2$ may be injected into the subsurface formation 120 for storage via the tubing string 122, although $CO_2$ may be injected in various other phases, within other fluids, compounds, etc. The tubing string 122 may be coupled to a tubing enclosed (or encased) conductor (TEC) line 118. The TEC line 118 may include an electrical line to convey power downhole, and the TEC line 118 may include a communications line. Some implementations of the TEC line 118 may include a fiber optic cable. The TEC line 118 may be coupled with one or more sensors 125 along its length that are welded in place along a surface the tubing string 122. In some implementations, the sensors 125 may be welded to an exterior of the tubing string 122 prior to the tubing string 122 being conveyed into the wellbore 112. At least a portion of the wellbore 112 may be cemented, solidifying the tubing string 122, sensors 125, and TEC line 118 in place.

The TEC line 118 may be configured to pass through one or more packers 115 and couple with one or more flow control devices 117. In some implementations, the flow control devices 117 may include fracture sleeves, interval control valves (ICVs), phase valves, electric flow control valves, any other type of downhole flow control valve, a ball baffle system, an inflow control device (ICD), an autonomous inflow control device (AICD), other autonomous inflow control devices, etc. The flow control device 117 may be configured to control injection and/or production into/from one or more formation zones, although other device configurations may be used. In some implementations, the flow control devices 117 may include a cross-coupling clamp on their exterior. The cross-coupling clamp may include a cable passthrough that guides the TEC line 118 along a path parallel to the tubing string 122 and provides stabilization for when the tubing string 122, TEC line 118, and sensors 125 are cemented in the wellbore 112. While FIG. 1 depicts the sensors 125 and TEC line 118 as cemented between the tubing string 122 and the wellbore 112, other configurations may also be possible. For example, the sensors 125 and TEC line 118 may alternatively be positioned within a cemented region 113 between a casing string 116 and the subsurface formation 120. However, the sensors 125 and TEC line 118 may be coupled to and cemented with any suitable downhole tubular. Other locations for placement of the sensors 125 and TEC line 118 may be possible.

The well system 100 may further include the surface equipment 105. The surface equipment 105 may comprise a wellhead, a choke, one or more production vessels, a power generator, a compressed air unit, one or more injection pumps, other equipment items, etc. In some implementations, the TEC line 118 may be coupled with the surface equipment 105. The one or more injection pumps of the surface equipment 105 may facilitate $CO_2$ injection, one or more generators may provide power to the TEC line 118, etc. A computer 150 may also be coupled to the surface equipment 105 and the TEC line 118. In some implementations, the computer 150 may be configured to receive measurements from the sensors 125 via the TEC line 118 and output commands to the flow control devices 117. For example, the sensors 125 may be pressure and temperature sensors configured to monitor pressure and temperature measurements during and after $CO_2$ injection. These pressure and temperature measurements may be sent to the computer 150 in real-time, at designated time intervals, etc. However, other functionalities of the sensors 125 and the computer 150 may be possible.

Example Downhole Sensor

Figure 2:
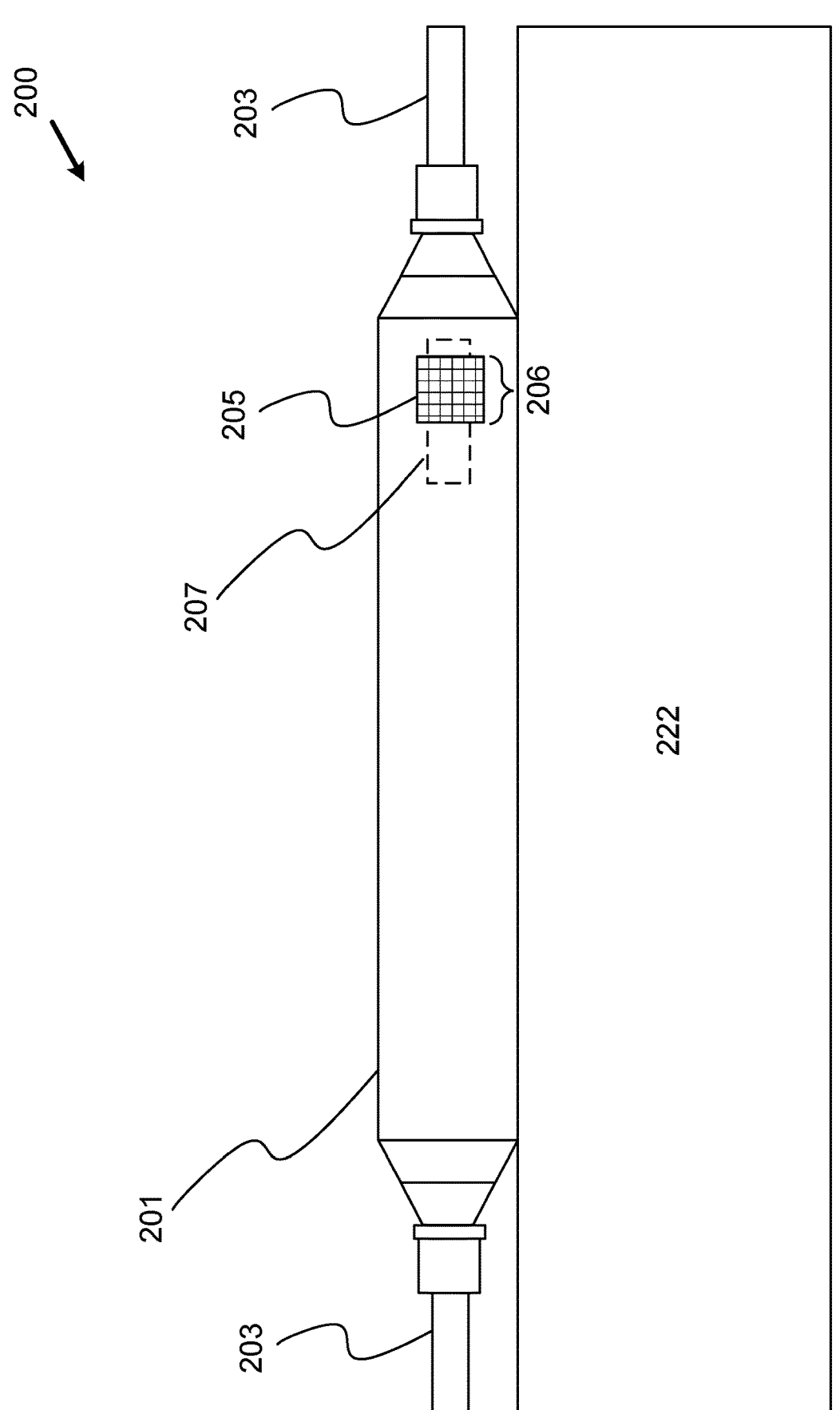
FIG. 2 is a schematic diagram depicting an example downhole sensor, according to some implementations.

FIG. 2 is a schematic diagram depicting an example downhole sensor 200, according to some implementations.

The downhole sensor 200 may be similar to each of the sensors 125 from FIG. 1. As shown in FIG. 1, multiple of the downhole sensor 200 may be included in a sensor array.

In some implementations, the downhole sensor 200 may be an integrated pressure and temperature sensor configured for use in a subsurface environment. The downhole sensor 200 may be coupled to a TEC line 203 similar to the TEC line 118 of FIG. 1. The downhole sensor 200 may include a sensor housing 201 welded to a tubular 222. The tubular 222 may be part of a cemented casing string similar to the casing string 116, a cemented tubing string similar to the tubing string 122 of FIG. 1, etc. The downhole sensor 200 may include an inlet port 206. The inlet port 206 may include an inlet filter 205 configured to prevent cement ingress and permit the flow of a pore fluid into the inlet port 206. In some implementations, the inlet filter 205 may include a mesh barrier of 21 microns, although other filtering media, mesh sizes, screens, etc. may be used. Within an interior of the sensor housing 201 and behind the inlet filter 205 is an optical sensor 207. In some implementations, the optical sensor 207 may be a micro integrated computational element (ICE) sensor. However, the optical sensor 207 may include any other sensing device suitable for $CO_2$ detection, configured for placement within the sensor housing 201, and configured to relay signals via the TEC line 203. The optical sensor 207 may be an optical computational element configured to perform optical measurements on pore fluid that has entered the inlet port 206. The optical sensor 207 is explained with additional detail in FIG. 3. In some implementations, multiple (e.g., two or three, although more may be possible) micro-ICE sensors may be included within the sensor housing 201.

Example Optical Sensor

Figure 3:
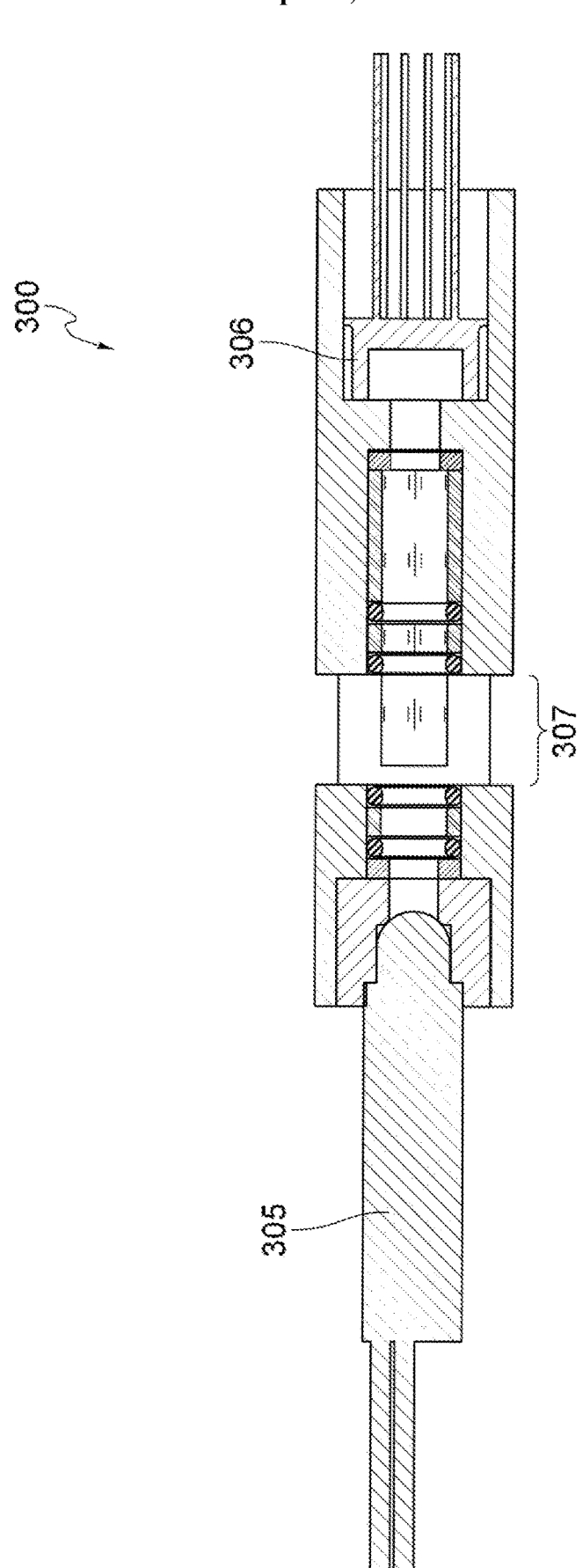
FIG. 3 is an illustration of an example optical sensor, according to some implementations.

FIG. 3 is an illustration of an example optical sensor 300, according to some implementations. The optical sensor 300 may be similar to the optical sensor 207 of FIG. 2. For example, the optical sensor 300 may be a $CO_2$ sensing micro-ICE sensor, although other sensor configurations (e.g., non-micro-ICE sensing devices) may be possible. In some implementations, the optical sensor 300 may be a micro-ICE sensor configured to sense a substance, element, compound, molecule, etc. other than carbon dioxide. For example, the optical sensor 300 may be configured to detect and measure a quantity of methane, ethane, propane, butane-pentane, C6+, C6+ Saturates fraction, C6+ Aromatics fraction, C6+ Resins fraction, C6+ Asphaltenes fraction, water, hydrogen, helium, etc. in the pore fluid. In some implementations, the optical sensor 300 (or each optical sensor in an array) may be configured to measure a single component of a pore fluid in a cemented wellbore, similar to the wellbore 112 of FIG. 1. Some implementations may include one or more optical sensors 300 that are configured to measure more than one component of a pore fluid in a cemented wellbore. For example, the optical sensor 300 may detect more than one component (e.g., two or three components, although more may be possible) of the pore fluid, although this may result in a larger device. Other implementations may utilize multiple of the optical sensor 300, where each optical sensor is configured to detect a single component of the pore fluid. In some implementations, one downhole sensor may include an optical sensor 300 configured to detect $CO_2$, and a different downhole sensor may include an optical sensor configured instead to detect a different fluid such as helium. However, other sensor configurations and combinations thereof may be possible.

For example, the optical sensor 300 may be used to measure multiple components within a fluid steam at a surface of the wellbore 112 for surface pre-injection monitoring, brine production, pre-injection testing, etc. The optical sensor 300 may be included in a cemented sensor array, although some implementations of the optical sensor 300 may be incorporated into an uncemented sensor array. For example, one or more optical sensors or similar sensing devices may be used for fluid detection in-line with a flow path through a tubular such as the casing string 116, tubing string 122, etc. Some implementations of this uncemented optical sensor may be positioned within an interior of its respective tubular to provide feedback regarding a composition of an injected fluid. Multiple in-line sensors may form an uncemented sensor array within the tubular. In some implementations, the uncemented, in-line configuration of the optical sensor 300 may also be configured to detect a phase of the injected fluid (e.g., injected $CO_2$).

The optical sensor 300 may include a light source 305 configured to shine light through the optical sensor 300. Gaseous $CO_2$, dissolved $CO_2$, carbonic acid, etc. may enter the optical sensor 300 via an inlet 307. A receiver medium 306 may receive the light rays emitted by the light source 305. This may include infrared light, although other light media may be used. The receiver medium 306 may be configured, for example, to deduce a presence and amount of dissolved $CO_2$ and/or carbonic acid. This may be achieved through optical spectroscopy, where the optical signatures received by the receiver medium 306 are compared to known optical signatures of various components/substances that may be present in the pore fluid. The computer 150 may include the known optical signatures, and measurements from the optical sensor 300 may be relayed to the computer 150 via the TEC line 118 to make the determination. Some implementations of the optical sensor 300 may include computerized functionality to detect and measure a component of the pore fluid without communicating with the computer 150.

The computer 150 may be configured to perform multivariate optical computing based on measurements from the optical sensor 300. The computer 150 may include one or more processors which may be operated to determine the carbon dioxide (or other substance) concentration of the pore fluid through the application of processing techniques. In some implementations, the processing techniques include any known computational method. In another implementation, the processing techniques may be selected from the group of least squares analysis, partial least squares regression (PLS), multivariate optical element (MOE), principal component analysis (PCA), principal component regression (PCR), multiple linear regression (MLR), classical least squares (CLS), analysis of variance (ANOVA), varimax rotation, singular value decomposition (SVD), multivariant curve resolution (MCR), Eigenvector Projection, chemometric techniques, mixture analysis, etc. and any combination thereof. Other processing techniques may also be possible.

In a CCUS well, the optical sensor 300 may be configured to identify and quantify other compounds containing $CO_2$, as well as other phases of $CO_2$. For example, the optical sensor 300 may be capable of identifying and quantifying dissolved $CO_2$, aqueous carbonic acid, etc. For permanent monitoring in a CCUS well, a downhole sensor array may include multiple pressure and temperature sensor housings including one or more individual micro-ICE optical sensors similar to the optical sensor 300. This sensor array may be cemented in the wellbore, and this sensor array is described with additional detail in FIG. 4

Example Sensor Array

Figure 4:
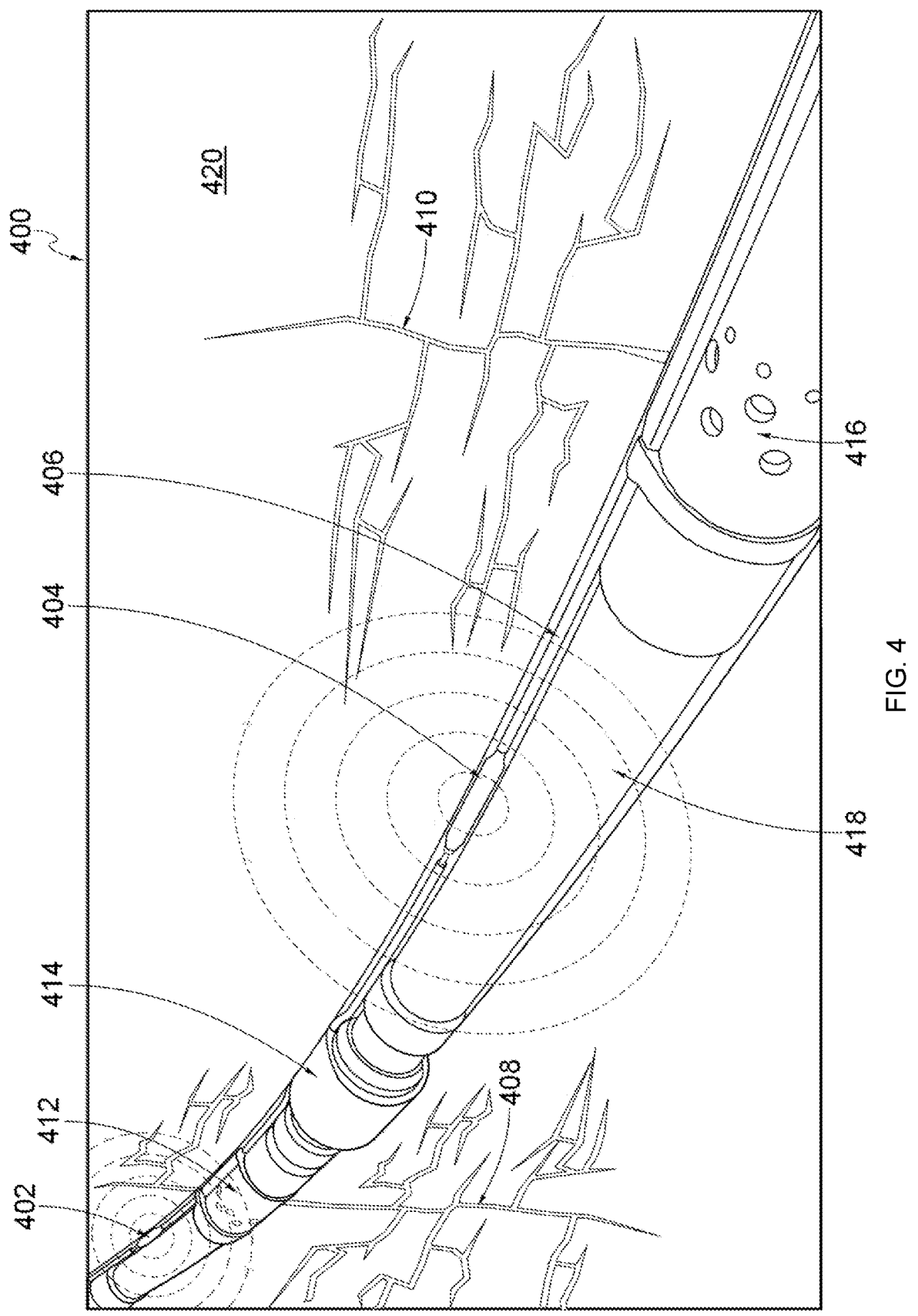
FIG. 4 is a schematic diagram depicting an example sensor array, according to some implementations.

FIG. 4 is a schematic diagram depicting an example sensor array 400, according to some implementations. FIG. 4 may be described with reference to FIGS. 1-3. A tubular 418 may be placed within a wellbore drilled through a subsurface formation 420. Some implementations of the tubular 418 may be similar to the tubular 222 of FIG. 2. The tubular 418 may include a packer 414 similar to the packer(s) 115. The tubular 418 may also include flow control devices 412 and 416, each similar to the flow control device 117 of FIG. 1. The packer 414 may provide fluidic separation between two treatment zones of the subsurface formation 420—a first fractured zone 408 and a second fractured zone 410. The first fractured zone 408 and the second fractured zone 410 may include a plurality of fractures to allow for fluid injection and storage. In CCUS wells, for example, carbon dioxide may be injected down the wellbore 112. The $CO_2$ may be injected into the fractures of the first fractured zone 408 via the flow control device 412 and similarly injected into the second fractured zone 410 via the flow control device 416 for storage. In some implementations, the $CO_2$ may later be produced via the respective flow control devices 412 and 416 to the surface for utilization.

Welded or otherwise coupled to the tubular 418 are downhole sensors 402 and 404. The downhole sensors 402 and 404 may be similar to the downhole sensor 200 of FIG. 2. The sensors 402 and 404 may be communicatively-coupled to one another (and additional downhole sensors) and the computer 150 of FIG. 1 via a TEC line 406. The TEC line 406 may be similar to the TEC line 118 of FIG. 1. The downhole sensors 402, 404 may be configured to measure pressure and temperature within the wellbore. The tubular 418, packer 414, flow control devices 412, 416, downhole sensors 402, 404, and the TEC line 406 may be cemented in place to provide permanent monitoring for the lifetime of the injection well.

In some implementations, the downhole sensors 402, 404 may each include one or more micro-ICE optical sensors, similar to the optical sensor 300. However, other sensing devices may also be used. The downhole sensors 402, 404 and their respective sensing devices within may be communicatively coupled to a computer at the surface similar to the computer 150. The computer 150 may include a reservoir model configured to receive pressure and temperature measurements from the downhole sensors 402, 404 in real-time. These pressure and temperature measurements from the downhole sensors 402,404 and $CO_2$ measurements from the sensing devices within may be relayed to the computer 150 to update a reservoir model of the $CO_2$ storage reservoir. The sensors 402 and 404 may also provide additional data to the computer 150, such as location and orientation data for each sensor in the array. The location and orientation data of the sensors 402, 404 may be utilized in the reservoir model (described in FIG. 5) for a multitude of purposes.

Other sensor configurations may be used to detect other materials that may indicate damage to cement in the wellbore, how fluids travel through the CO2 storage reservoir, etc. For example, the micro-ICE optical sensors and/or other sensing devices may instead or additionally be configured as helium-detecting optical computational elements to detect helium within the pore fluid. Because helium molecules are smaller than carbon dioxide molecules, helium may travel through the subsurface formation 420 faster than CO2 and may be detected earlier. This sensor configuration may provide early indications to the reservoir model on how CO2 might travel through the storage reservoir, and adjustments to injection operations and/or equipment may be made much earlier to anticipate and ultimately mitigate future cement damage.

Some implementations of the sensors 402, 404 may include micro-ICE optical sensors and/or other sensing devices configured for other underground fluid storage and monitoring applications other than $CO_2$ injection. For example, the sensors 402, 404 may be configured to detect hydrogen ($H_2$) for use in hydrogen storage applications, configured to detect methane ($CH_4$) for use in methane storage applications, etc. However, some implementations of the sensors 402, 404 may be positioned within depleted gas reservoirs, salt caverns, etc. to monitor hydrogen injection and storage as well. The storage applications may not be limited to fluid storage within the pore space of one or more subsurface formations. For example, other implementations of the sensors 402, 404 may be configured to monitor hydrogen leakage from hydrogen storage applications within one or more vertically-positioned tubulars configured to store hydrogen. The tubulars may be positioned at the surface or within a borehole. The sensors 402, 404 may include $H_2$ sensing devices configured to detect and measure and quantity of hydrogen leakage from the vertically-positioned tubulars. In some implementations, the $H_2$ sensing device may include a below-grate $H_2$ detector configured to identify leakage from tubulars. However, other configurations of the sensors 402 and 404 may be possible.

In some implementations, the sensors 402, 404 may also include sensing devices for monitoring, detection and quantification of fluids generated via other processes. These processes may produce one or more fluids to be stored in a subsurface formation, within a storage vessel of any suitable geometry (including one or more tubulars), etc. Some implementations of the sensors 402, 404, may be cemented, and other implementations of the sensors 402,404 may be uncemented. For example, the sensors 402, 404 and sensing devices within, such as the optical sensor 300, may be configured to detect and quantify $CO_2$, $H_2$, and $CH_4$ during methane pyrolysis, to detect and quantify $H_2$ and $CH_4$ during methane plasmalysis, to detect and quantify $H_2$ and oxygen ($O_2$) during water electrolysis, to detect and quantify biomethane and hydrogen sulfide ($H_2S$) produced via microbial action, etc. Other permanent sensing applications may be possible.

The microbial action may be quantified based on the detection and quantity of biomethane observed by micro-ICE sensing devices within the sensors 402, 404. The production of biomethane via microbes within an anaerobic digester vessel, within a subsurface gas storage formation, etc. may be monitored via the sensors 402, 404. Data related to the microbial activity may be transmitted to a user interface of a computer similar to the computer 150 via a communication line similar to the TEC line 406. In some implementations, the microbial activity may induce a positive or a negative reaction in an underground storage formation, and the sensors 402, 404 may allow a user to monitor the reaction as product fluids, such as $H_2S$, water, and $CH_4$, may be generated through the reaction. Other components such $H_2$, $CO_2$, etc. may also be measured downhole via at least the sensors 402, 404 during the above-described reaction.

Example System Architecture

Figure 5:
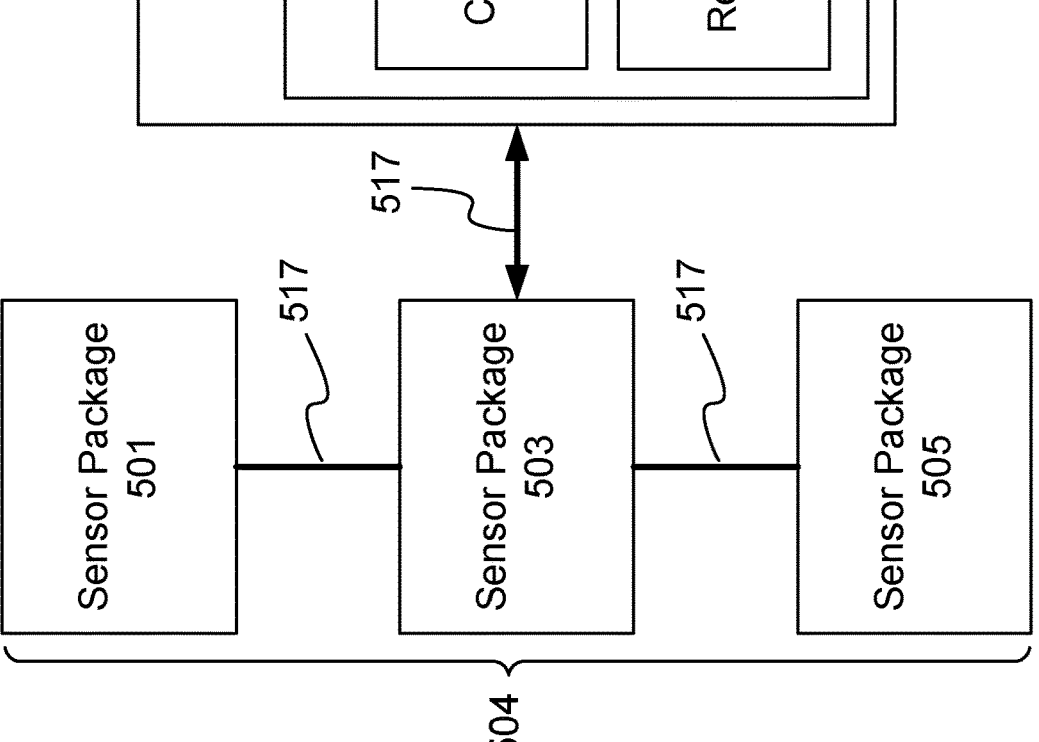
FIG. 5 is a block diagram depicting an example system architecture, according to some implementations.

FIG. 5 is a block diagram depicting an example system architecture 500, according to some implementations. The system architecture 500 may include various devices and computerized functionalities used to mitigate cement damage during $CO_2$ injection into a CCUS well. The system architecture 500 may include sensor packages 501, 503, and 505 which together form a sensor array 504 in a cemented wellbore. Each sensor package may include at least a downhole integrated pressure and temperature sensor similar to the downhole sensor 200. Each sensor package may also include at least one sensing device micro-ICE optical sensor, similar to the optical sensors 207 and 300. In some implementations, the sensing device may be a micro-ICE sensor configured to detect $CO_2$, although other configurations may be possible. The sensor packages 501-505 may be cemented between a casing string and a wellbore, a tubing string and the wellbore, etc. The sensor packages 501, 503, and 505 may be communicatively and electronically coupled via a TEC line 517. More sensor packages may be included, and additional sensors may be included in each sensor package. In some implementations, some sensor packages may include or otherwise be communicatively coupled to a three-phase flow meter in the wellbore 112. Measurements from a micro-ICE optical sensor may be cross-referenced or combined with measurements from the three-phase flow meter to perform multivariate optical computing. Therefore, both a presence and the phase of the detected $CO_2$ may be determined.

The TEC line 517 may also couple the sensor packages 501-505 to a computer 507 which may be similar to the computer 150 of FIG. 1. The computer 507 may include computerized functionalities to model one or more subsurface formations of the $CO_2$ storage reservoir, to predict an extent of cement damage in the CCUS wellbore based on sensor package measurements, to output commands that may mitigate further damage, etc. For example, the computer 507 may include a cement life model 509 and a reservoir simulator 511.

The sensor packages 501-505 may be positioned at various measured depths along the wellbore of the CCUS well. For example, sensor package 501 may be positioned higher in the wellbore 112 at a shallower true vertical depth (TVD) than the sensor package 503, and the sensor package 503 may be positioned higher than the sensor package 505 along the TEC line 517. However, other configurations may be possible. In some implementations, data from one or more sensor packages positioned in a sentinel well, a monitoring well, an offset well, etc. may also be relayed to the computer 507.

In the example system architecture 500, the sensor packages 501-505, the computer 507, the cement life model 509, and the reservoir simulator 511 may be used to locate an injected $CO_2$ plume during $CO_2$ injection. The CO2 plume may refer to the physical extent of the injected $CO_2$ stream in three dimensions, including both the free-phase and dissolved fluid within the subsurface. During injection, high-pressure (e.g., greater than 1,000 psi) $CO_2$ from an injection tool may push back an existing $CO_2$ plume in the storage reservoir. This $CO_2$ may be injected below a caprock of each storage zone. In some implementations, at least one of the sensor packages 501-505 may be positioned above the cap rock of its respective nearby storage zone. For example, the downhole sensors 402 and 404 are positioned above the first and second fractured zones 408, 410, respectively. However, more sensor packages may be placed in the cemented wellbore. If a micro-ICE sensor within a sensor package detects the presence of $CO_2$, this may indicate that either cement integrity, caprock integrity, or $CO_2$ injection viability is in jeopardy. $CO_2$ detection may be confirmed by both the micro-ICE optical sensor and by other downhole measurements from each sensor package. For example, $CO_2$ infiltration into the cement of the wellbore 112 may induce an increase in pressure and a decrease in temperature at the proximate sensor package. Carbon dioxide detection within the cement may indicate that the CO2 plume has reached and potentially exceeded the fractured zone's caprock.

The sensor packages 501-505 may also be configured for sensing $CO_2$ migration even when downhole cement integrity remains intact. For example, downhole cement may retain sufficient permeability and porosity such that pressure transmission between subsurface zones may occur during fluid injection. One or more sensor packages of the sensor packages 501-505 may be configured to detect $CO_2$ or other fluid migration into undesired regions such as an isolated zone (isolated via one or more packers), a region above the caprock, etc. even when the cement is intact. Some implementations of the sensor packages 501-505 may be uncemented to detect injection fluid leakage.

The reservoir simulator 511 and the cement life model 509 may be physics-based models, data-based models, deep learning models, or any combination thereof. Some implementations of the cement life model 509 and reservoir simulator 511 may utilize machine learning models, neural networks, etc., although traditional computational models may also be used. The reservoir simulator 511 and cement life model 509 may receive measurements from the sensor packages 501-505 via the TEC line 517. The reservoir simulator 511 and cement life model 509 may also receive micro-ICE measurements, pressure data, and/or temperature data from one or more nearby monitoring wells. Together, the reservoir simulator 511 and cement life model 509 may be referred to as the reservoir model 510. For example, the cement life model 509 and reservoir simulator 511 may be integrated into the singular reservoir model 510 within the computer 507.

Sensor data of $CO_2$ ingress into wellbore cement may provide information about the $CO_2$ storage reservoir which may be used to train the reservoir simulator 511 and the cement life model 509. The reservoir simulator 511 may simulate subsurface properties of one or more subsurface formations including the $CO_2$ storage reservoir, one or more wellbores, an injection profile of $CO_2$ into the storage reservoir, other flow profiles, etc. Data obtained via the sensor packages 501-505 may be compared to the simulated data within the reservoir simulator 511. The reservoir simulator 511 may be adjusted as needed based on the measured sensor data. In some implementations, the received data may update the reservoir simulator 511 in real-time. This may help improve the injection profile through the wellbore and may enable cement health issues to be mitigated before they arise. Preventing potential damage to the cement in the wellbore may thereby extend the life and value of the storage reservoir.

Some implementations of the reservoir simulator 511 may simulate a predicted propagation of the carbon plume in the subsurface. The reservoir simulator 511 may output a three-dimensional simulation that models a travel of the plume based on measurements from the sensor packages 501-505. Sensor data from the sensor packages 501-505 may also allow the reservoir simulator 511 to determine an extent of $CO_2$ leakage out of the storage reservoir, how far the leaked $CO_2$ has traveled (based on multiple sensor readings), and a duration of how long the leak has been occurring.

In some implementations, the cement life model 509 may be in communication with the reservoir simulator 511. The cement life model 509 may be configured to predict an extent of damage and/or the cement integrity of the wellbore 112 based on measurements from the sensor packages 501-505. In some implementations, output from the cement life model 509 may induce changes within the reservoir simulator 511. Vice versa, updates to the reservoir simulator 511 may cause the cement life model 509 to update its predictions regarding cement integrity. Suggestions from the cement life model 509 and a simulated reservoir from the reservoir simulator 511 may be output to a user interface 519 in real time. Pressure and temperature gauge data, $CO_2$ detection notifications, pressure and temperature changes beyond a threshold, and notifications of other wellbore events may also be output to the user interface 519. A wellbore event may be defined as a property measurement, a rate of change of a property measurement, etc. falling outside of user-defined limits provided to the cement life model 509 and reservoir simulator 511. The property may include an injection pressure, estimated formation pressure, temperature, carbon dioxide concentration, etc.

The reservoir model 510 may utilize both the cement life model 509 and the reservoir simulator 511 simultaneously upon $CO_2$ detection. For example, the cement life model 509 may intake measurements from the sensor packages 501-505 (both those that have detected $CO_2$ and those which have not) to determine a severity of cement carbonation of the wellbore 112. For example, an extent of carbonation of the wellbore cement may be estimated based on pressure and temperature measurements, measured $CO_2$ quantity, one or more fluid ratios (e.g., ratio of $CO_2$ to other components) within the pore fluid, an estimated duration of $CO_2$ leakage based on predictions from the reservoir simulator 511, etc. The cement life model 509 may predict cement damage and a remaining operational life of the wellbore cement. The cement life model 509 may also be used to predict how long the current pumping conditions may be continued without causing severe loss of estimated life of the cement. Some scenarios may permit additional $CO_2$ injection.

The reservoir model 510 may output an updated injection procedure, suggest alterations to the injection profile, output commands to one or more devices, etc. based on the measured data from the sensor packages 501-505. For example, the reservoir model 510 may output commands to injection equipment 513 and at least one flow control device 515 via the computer 507 and the TEC line 517. The injection equipment 513 may include one or more pumps, chokes, valves, etc. at the surface that, when adjusted, may alter the flow profile of the injected $CO_2$. The flow control device 515 may be similar to the flow control devices 412, 416, etc. The flow control device 515 may include a fracture sleeve, a choke sleeve, an ICV, an autonomous ICV (AICV), a phase valve, etc. The reservoir model 510 may output commands that implement a remedial action, and the computer 507 may send these commands to the injection equipment 513 and the flow control device 515 (one is shown, but multiple flow control devices may receive commands simultaneously). The remedial action may be performed via user input or autonomously. In some implementations, remedial actions may be output based on exceeding one or more thresholds relating to predicted cement damage, $CO_2$ infiltration, maintaining a desirable injection profile, etc.

Remedial action may comprise generating an updated injection profile by the reservoir simulator 511 to achieve a new cement life scenario output by the cement life model 509. This scenario may extend the life of the wellbore cement compared to current injection parameters. For example, the cement life model 509 may predict the influence of the pumping/injection procedure on the cap rock integrity or $CO_2$ migration for the new scenario. $CO_2$ detection and other measurements obtained by at least one sensor package may indicate that the $CO_2$ injection path is now different than the simulated injection profile of the reservoir simulator 511. If the cement life model 509 predicts a sub-optimal outcome based on current injection parameters, then injection operations may be changed to accomplish the goal of halting cement carbonation. The reservoir model 510 may recommend changing pumping parameters at the injection equipment 513 such as pump rate, or the reservoir model 510 may recommend to begin injection at the next location/stage. These recommendations may be output to the user interface 519. For non-injection storage operations, the reservoir model 510 may be configured to output other remedial commands.

The reservoir model 510 may also output commands to the flow control device 515 based on sensor readings from wellbores other than the injection wellbore. For example, upon $CO_2$ detection by a sensing device, a pressure rise, and/or a temperature decrease beyond set thresholds in a cemented monitoring well, the reservoir model 510 may output a command to a flow control device such as a fracture sleeve to close, similar to the flow control device 412. However, the reservoir model 510 may be configured to respond to other scenarios with input from other sensors, sensor packages, other nearby wellbores, etc. Generally, data from the sensor packages 501-505 may be fed as input data into the reservoir model 510. The reservoir simulator 511 and cement life model 509 may generate predictions and update their own parameters, weights, algorithms, etc. based on the input data. Input data may be received in real-time, received at regular intervals, etc. The cement life model 509 and the reservoir simulator 511 may communicate with one another to determine one or more updates to the current injection operation. The reservoir model 510 may output commands to at least one of the injection equipment 513, one or more flow control devices 515, etc. to implement a real-time injection decision. Some implementations of the reservoir model 510 may output these commands and initiate remedial measures autonomously. In other implementations, the reservoir model 510 may output suggestions to a user interface 519, and the user may initiate remedial measures to limit cement damage. Other data including sensor data, an updated injection profile, cement life projections, etc. may be output to the user interface 519 via the reservoir model 510.

Other remedial actions may include injecting one or more sealing agents to seal a breach in the wellbore cement. The cement life model 509 may predict the effect of injecting the sealing agents, and the reservoir simulator 511 may update the injection profile based on the cement life model's prediction. Yet another example remedial action may include autonomously shutting in one or more zones based on a phase of detected $CO_2$. For example, the flow control devices 412 and 416 may be phase valves. If a micro-ICE sensor, for example, determines that detected $CO_2$ has undergone a phase change (e.g., from the supercritical to a vapor phase), this measurement may trigger the phase valve 416 to close. Alternatively, a phase change of the $CO_2$ may cause a pressure or temperature change, and this signature may be detectable by the one of the sensor packages of the sensor array 504. The signature of the pressure and/or temperature change due to the phase change may be used to trigger a respective phase valve.

Figure 6:
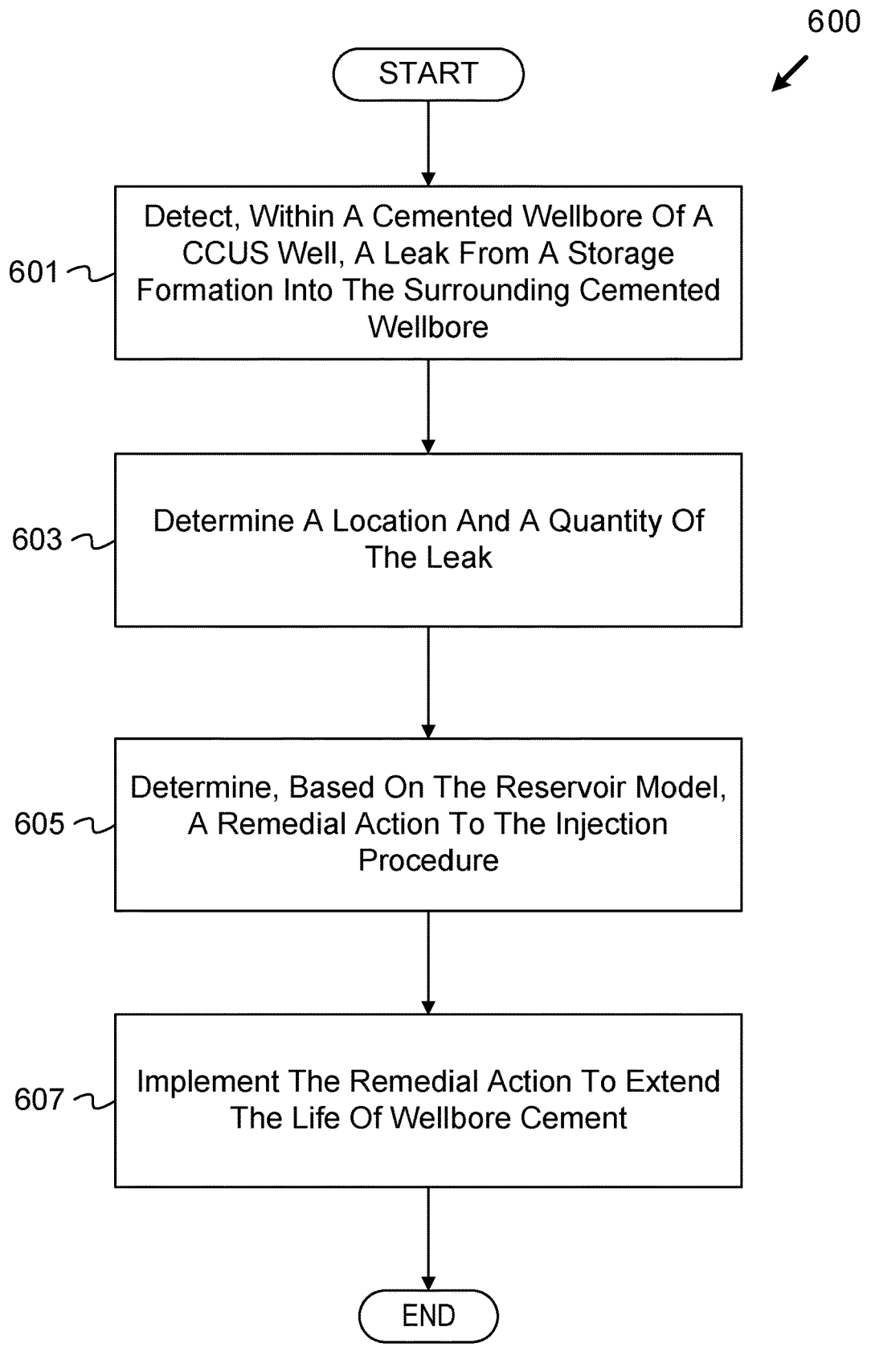
FIG. 6 is a flowchart of operations for mitigating damage to the cement of a CCUS wellbore, according to some implementations.

FIG. 6 is a flowchart 600 of operations for mitigating damage to the cement of a CCUS wellbore, according to some implementations. Operations of the flowchart 600 may be performed in part by software, firmware, hardware, or a combination thereof. Such operations are described with reference to FIGS. 1-5. However, such operations may be performed by other systems or components. The operations of the flowchart 600 begin at block 601.

At block 601, one or more permanent sensors may detect, within a cemented wellbore of a CCUS well, a leak from a storage formation into the surrounding cemented wellbore. For example, at least one of the sensor packages 501-505 may determine that $CO_2$ has leaked out of a storage reservoir and migrated into a shallower zone, the $CO_2$ has migrated into the surrounding wellbore, etc. $CO_2$ detection may occur when a micro-ICE sensor or other suitable sensing device detects the optical signature of one or more carbon-based chemical species, when pressure and temperature changes match an expected signature for carbon intrusion, etc. The measurements may be sent to the computer 150 in real time. Monitoring for $CO_2$ or other targeted substances may occur throughout the lifetime of the CCUS wellbore. Flow progresses to block 603.

At block 603, the location and quantity of the leak may be determined. For example, the computer 507 may use measurements from the sensor array 504 to make this determination. Determining the location and quantity of the leak may include estimating an extent of cement damage based on measurements via the sensor array 504 including the sensor packages 501-505. The extent of cement damage may also be determined via output from the reservoir simulator 511 and cement life model 509. In some implementations, determining the location of the leak may include helium injection into the storage formation. Helium molecules are smaller than $CO_2$ molecules and travel quickly through the fractures and pore spaces of subsurface formations. The injected helium may be detected by one or more micro-ICE sensors or other sensing devices in the sensor array 504 configured to detect helium, and this may reveal one or more travel paths, leaks, etc. in the storage reservoir. This may allow an operator at the surface to predict anticipated travel paths of injected fluids such as $CO_2$ through the reservoir ahead of time and which areas of wellbore cement may be most susceptible to carbonation.

A leak may also be indicative of other problems in the CCUS well outside of cement degradation. For example, a $CO_2$ leak located at a higher location in the wellbore than the caprock of its suspected zone of injection that continues to leak for an elapsed time after injection has ceased may indicate that the injection procedure requires change. For example, detected leakage from the storage formation after an elapsed time of paused injection may indicate the storage formation is near capacity. Changes to the injection procedure may be aimed at avoiding an overpressurization of the storage formation. An overpressurization incident could plug the storage reservoir, where the $CO_2$ plume in the overpressurized formation may prevent additional injected fluid from moving into the storage formation. Some instances of overpressurization without intervention may cause an operating pressure of the injection string to exceed the storage reservoir's fracture pressure. Either of the above scenarios may cause damage to the storage reservoir. Therefore, a detected leak may necessitate remedial action. Flow progresses to block 605.

At block 605, the computer 507 may determine, based on the reservoir model 510, a remedial action to the injection procedure. For example, the remedial action may be based on a set of equipment parameters that prolong the operating lifespan of the wellbore cement. In some implementations, the cement life model 509 may determine one or more alterations to the injection procedure which may be sent to the user interface 519. The reservoir simulator 511 may simulate the proposed injection procedure and output this to the user interface 519 as well. The reservoir model 510 may output commands for autonomous intervention via one or more processors of the computer 507 to the injection equipment 513, flow control device(s) 515, etc. via the TEC line 517. Flow progresses to block 607.

At block 607, the remedial action to extend the life of the wellbore cement is implemented. The remedial action may be induced from measurements via the sensor array 504 inside the injection wellbore 112 or from sensors in nearby monitoring wells, sentinel wells, etc. An operator or user may implement the remedial action. This remedial action may also be implemented autonomously via commands from the reservoir model 510. The remedial action may vary an injection profile into the CCUS well to prevent a $CO_2$ plume from migrating outside of the desired storage formation and extend the life of wellbore cement. In some implementations, the remedial action may include shutting in the injection well. Flow of the flowchart 600 ceases.

Example Computer

Figure 7:
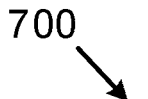
FIG. 7 is a block diagram depicting an example computer, according to some implementations.

FIG. 7 is a block diagram depicting an example computer 700, according to some implementations. The computer 700 includes a processor 701 (possibly including multiple processors, multiple cores, multiple nodes, and/or implementing multi-threading, etc.). The computer 700 includes memory 707. The memory 707 may be system memory or any one or more of the above already described possible realizations of machine-readable media. The computer 700 also includes a bus 703 and a network interface 705. The computer 700 may communicate via transmissions to and/or from remote devices via the network interface 705 in accordance with a network protocol corresponding to the type of network interface, whether wired or wireless and depending upon the carrying medium. In addition, a communication or transmission may involve other layers of a communication protocol and or communication protocol suites (e.g., transmission control protocol, Internet Protocol, user datagram protocol, virtual private network protocols, etc.).

The computer 700 may include a reservoir modeler 709 and a device controller 711 which may perform the operations described herein. For example, the reservoir modeler 709 may be configured to perform the above-described operations of the reservoir model 510, the reservoir model 510 including the reservoir simulator 511 and cement life model 509 of FIG. 5. The device controller may include computerized functionality to adjust the injection equipment 513 and the flow control device(s) 515 of FIG. 5 based on output from the reservoir modeler 709. In some implementations, the computer 700 may be similar to FIG. 1's computer 150 and FIG. 5's computer 507. The reservoir modeler 709 and the device controller 711 may be in communication. Any one of the previously described functionalities may be partially (or entirely) implemented in hardware and/or on the processor 701. For example, the functionality may be implemented with an application specific integrated circuit, in logic implemented in the processor 701, in a co-processor on a peripheral device or card, etc. Further, realizations may include fewer or additional components not illustrated in FIG. 7 (e.g., video cards, audio cards, additional network interfaces, peripheral devices, etc.). The processor 701 and the network interface 705 are coupled to the bus 703. Although illustrated as being coupled to the bus 703, the memory 707 may be coupled to the processor 701.

Example Method

Figure 8:
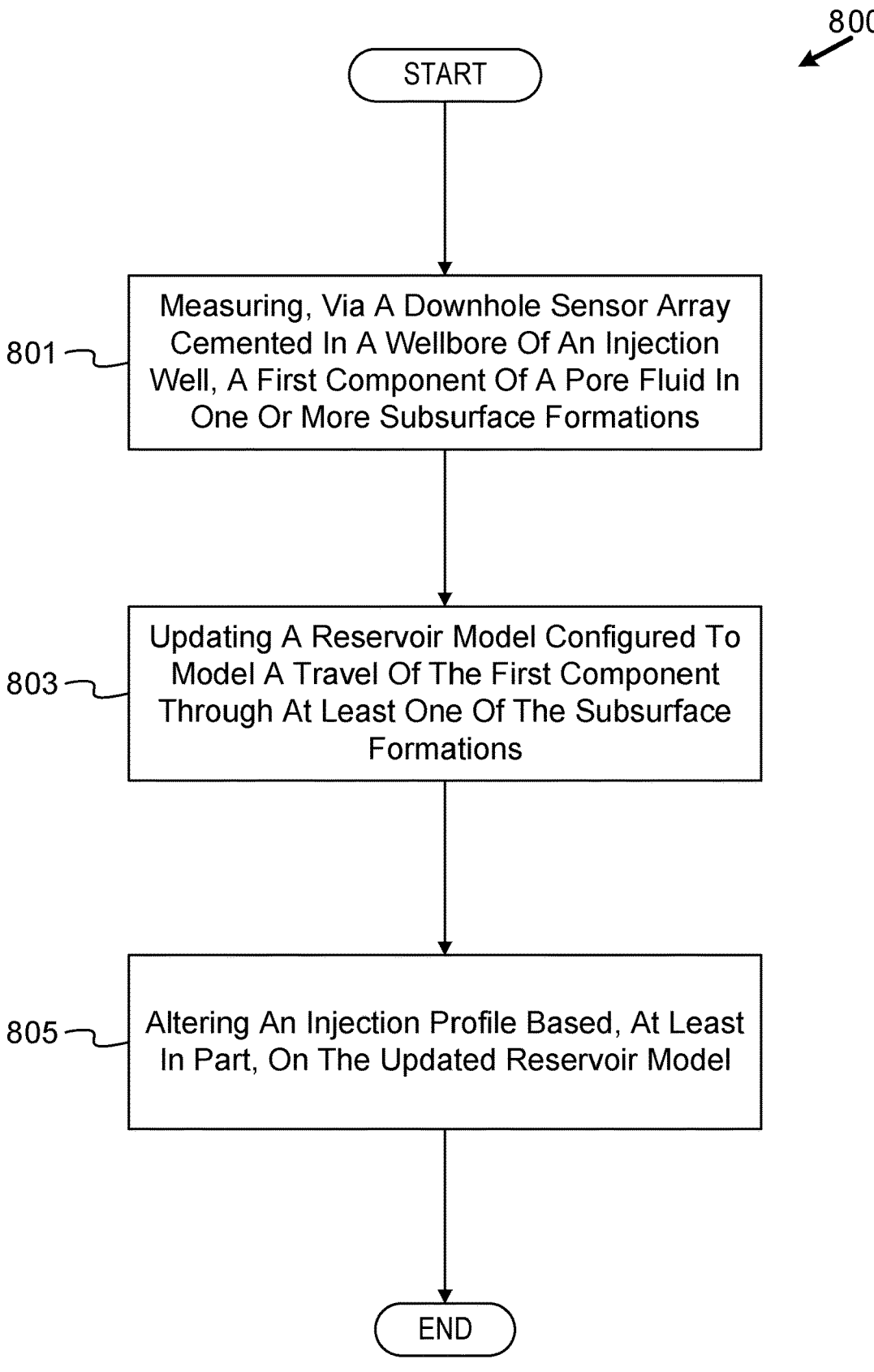
FIG. 8 is a flowchart depicting an example method, according to some implementations.

FIG. 8 is a flowchart depicting an example method, according to some implementations. Operations of a method 800 may be performed in part by software, firmware, hardware, or a combination thereof. Such operations are described with reference to FIGS. 1-7. However, such operations may be performed by other systems or components. The operations of the method 800 begin at block 801.

At block 801, the method 800 includes measuring, via the downhole sensor array 504 cemented in the wellbore 112 of an injection well, a first component of a pore fluid in one or more subsurface formations. For example, at least one sensor package 501-505 may be configured for permanent monitoring and detection of $CO_2$ in the wellbore 112 via a sensing device including, but not limited to, an optical computational element, various pressure, temperature, etc. sensors, and any combination thereof. For example, $CO_2$ may be detected by performing optical spectroscopy on pore fluid that enters the inlet 307 of the optical sensor 300. Pore fluid may be configured to enter the inlet 307 while cement ingress is halted via the inlet filter 205. Other configurations of the sensor packages 501-505 may be possible. Flow progresses to block 803.

At block 803, the method 800 includes updating a reservoir model 510 configured to model a travel of the first component through at least one of the subsurface formations. For example, the reservoir simulator 511 of the reservoir model 510 may be configured to simulate formation properties of a $CO_2$ storage reservoir, a predicted travel path for a $CO_2$ plume through the storage reservoir, an injection profile of the CO2, etc. The reservoir simulator 511 may be updated directly via measurements from the sensor packages 501-505, and/or the reservoir simulator 511 may be updated based on output from the cement life model 509. Other implementations of the reservoir model 510 may be configured to model a travel of the first component of a fluid in other fluid storage applications such as hydrogen storage, methane storage, etc. within a subsurface formation. Some implementations of the reservoir model 510 may be used for fluid detection with other storage media. Flow progresses to block 805.

As block 805, the method 800 includes altering an injection profile based, at least in part, on the updated reservoir model. For example, the cement life model 509 may propose an updated injection profile that may prolong the operating life of the wellbore cement, and the reservoir simulator 511 may tune its algorithm to reflect the updated injection profile. The reservoir model 510 may output commands via the computer 507 to at least one of the injection equipment 513 and the flow control device 515 for autonomous intervention. Alternatively or in addition, suggestions may be output to a user interface 519 for user-implemented intervention. Remedial action may be implemented to achieve the altered injection profile which may prolong the operating lifespan of the wellbore cement. Flow of the method 800 ceases.

Example Implementations

Implementation 1: A system comprising: an electrical line positioned proximate to one or more subsurface formations; and a permanent downhole sensor array coupled to the electrical line, the permanent downhole sensor array including one or more downhole sensors, each downhole sensor including: a first sensing device configured to detect at least a first component of a downhole fluid.

Implementation 2: The system of Implementation 1, further comprising: a tubular positioned in a wellbore of an injection well drilled through one or more subsurface formations, wherein the electrical line is coupled to the tubular, wherein the tubular, electrical line, and permanent downhole sensor array are cemented within the wellbore, wherein the first sensing device includes a first optical computational element configured to detect and quantify at least the first component of the downhole fluid within the wellbore for a lifetime of the injection well, and wherein the downhole fluid is a pore fluid of the one or more subsurface formations.

Implementation 3: The system of any one or more of Implementations 1-2, further comprising: a flow control device positioned proximate to a fractured zone of the wellbore and communicatively coupled to the first sensing device, wherein the flow control device is configured to close upon detection of the first component by the first sensing device.

Implementation 4: The system of any one or more of Implementations 1-3, further comprising: a processor; and a computer-readable medium having instructions executable by the processor, the instructions including: instructions to measure, via the permanent downhole sensor array cemented in the wellbore of the injection well, a quantity of the first component of the downhole fluid in one or more subsurface formations; instructions to update a reservoir model configured to model a travel of the first component through at least one of the subsurface formations; and instructions to alter an injection profile based, at least in part, on the updated reservoir model.

Implementation 5: The system of any one or more of Implementations 1-4, further comprising: instructions to assess a health of cement in the wellbore based, at least in part, on the quantity of the first component; and instructions to perform a wellbore operation to mitigate damage to the cement in the wellbore.

Implementation 6: The system of any one or more of Implementations 1-5, wherein each downhole sensor of the permanent downhole sensor array includes an inlet filter configured to allow entry of the downhole fluid and inhibit cement flow into each respective sensing device.

Implementation 7: The system of any one or more of Implementations 1-6, further comprising: a three-phase flow meter communicatively coupled with the first sensing device.

Implementation 8: The system of any one or more of Implementations 1-7, wherein the first sensing device is configured to detect and to measure at least a second component of the downhole fluid.

Implementation 9: The system of any one or more of Implementations 1-8, wherein each downhole sensor in the permanent downhole sensor array includes the first sensing device and a second sensing device, wherein the second sensing device is configured to detect a presence and measure a quantity of a second component of the downhole fluid.

Implementation 10: An apparatus comprising: a downhole sensor configured for placement proximate to one or more subsurface formations; and a first sensing device housed within the downhole sensor, the first sensing device configured to detect at least a first component of a downhole fluid.

Implementation 11: The apparatus of Implementation 10, wherein the downhole sensor is configured to be cemented in a wellbore of an injection well drilled through the one or more subsurface formations, wherein the first sensing device is configured to measure a quantity of the first component of the downhole fluid for a lifetime of the injection well, and wherein the downhole fluid is a pore fluid of the one or more subsurface formations.

Implementation 12: The apparatus of any one or more of Implementations 10-11, further comprising: at least a second sensing device housed within the downhole sensor, wherein the second sensing device is configured to detect a second component of the downhole fluid.

Implementation 13: The apparatus of any one or more of Implementations 10-12, wherein the first sensing device is configured to detect and to measure at least a second component of the downhole fluid.

Implementation 14: The apparatus of any one or more of Implementations 10-13, wherein the downhole sensor includes an inlet filter configured to allow entry of the downhole fluid and inhibit cement flow into the first sensing device.

Implementation 15: A method comprising: measuring, via a permanent downhole sensor array, a first component of a downhole fluid in one or more subsurface formations; and updating a reservoir model configured to model a travel of the first component through at least one of the subsurface formations.

Implementation 16: The method of Implementation 15, further comprising: injecting, via a wellbore of an injection well, the first component into the one or more subsurface formations; and altering an injection profile of the injection well based, at least in part, on the updated reservoir model, wherein the permanent downhole sensor array is cemented in the wellbore of the injection well.

Implementation 17: The method of any one or more of Implementations 15-16, wherein altering the injection profile of the injection well based, at least in part, on the updated reservoir model comprises altering the injection profile in real-time.

Implementation 18: The method of any one or more of Implementations 15-17, wherein measuring, via the permanent downhole sensor array cemented in the wellbore, the first component of the downhole fluid in the one or more subsurface formations comprises measuring a quantity of the first component using one or more sensing devices for a lifetime of the injection well.

Implementation 19: The method of any one or more of Implementations 15-18, further comprising: assessing a health of cement in the wellbore based, at least in part, on the measuring of the first component; and performing a wellbore operation to mitigate damage to the cement in the wellbore.

Implementation 20: The method of any one or more of Implementations 15-19, further comprising: injecting a second component into the one or more subsurface formations, wherein the second component travels through the one or more subsurface formations faster than the first component; detecting the second component at a location of the permanent downhole sensor array; updating the reservoir model based on the detection of the second component; and predicting a travel path of the first component based on the detection of the second component.

The various illustrative logics, logical blocks, modules, circuits, and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described throughout. Whether such functionality is implemented in hardware or software depends upon the particular application and design constraints imposed on the overall system.

The hardware and data processing apparatus used to implement the various illustrative logics, logical blocks, modules and circuits described in connection with the implementations disclosed herein may be implemented or performed with a general purpose single- or multi-chip processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor or any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more implementations, the functions and/or functionalities described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, e.g., one or more modules of computer program instructions stored on a computer storage media for execution by, or to control the operation of, a computing device.

If implemented in software, the functions and/or functionalities may be stored on or transmitted over as one or more instructions or code on a computer-readable medium. The processes of a method or algorithm disclosed herein may be implemented in a processor-executable instructions which may reside on a computer-readable medium. Computer-readable media includes both computer storage media and communication media including any medium that may be enabled to transfer a computer program from one place to another. Storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-Ray™ disc where disks usually reproduce data magnetically, while discs reproduce data optically with lasers. Combinations also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein but are to be accorded the widest scope consistent with this disclosure, the principles and the novel features disclosed herein.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described as acting in certain combinations and even initially claimed as such, one or more features from a claimed combination may in some cases be excised from the combination, and the claimed combination may be directed to a sub-combination or variation of a sub-combination.

While operations are depicted in the drawings in a particular order, this should not be understood as requiring that such operations be performed in the particular order shown or in sequential order, or that all illustrated operations be performed, to achieve desirable results. Further, the drawings may schematically depict one more example process in the form of a flow diagram. However, some operations may be omitted and/or other operations that are not depicted may be incorporated in the example processes that are schematically illustrated. For example, one or more additional operations may be performed before, after, simultaneously, or between any of the illustrated operations. In certain circumstances, multitasking and parallel processing may be advantageous. Moreover, the separation of various system components in the implementations described should not be understood as requiring such separation in all implementations, and the described program components and systems may generally be integrated together in a single software product or packaged into multiple software products. Additionally, other implementations are within the scope of the following claims. In some cases, the actions recited in the claims may be performed in a different order and still achieve desirable results.

Unless otherwise specified, use of the terms "up," "upper," "upward," "uphole," "upstream," or other like terms shall be construed as generally away from the bottom, terminal end of a well; likewise, use of the terms "down," "lower," "downward," "downhole," or other like terms shall be construed as generally toward the bottom, terminal end of the well, regardless of the wellbore orientation. Use of any one or more of the foregoing terms shall not be construed as denoting positions along a perfectly vertical axis. In some instances, a part near the end of the well can be horizontal or even slightly directed upwards. Unless otherwise specified, use of the terms "subsurface formation" or "subterranean formation" shall be construed as encompassing both areas below exposed earth and areas below earth covered by water such as ocean or fresh water.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" may be infringed with only one of the listed items, multiple of the listed items, and one or more of the items in the list and another item not listed. As used herein, a phrase referring to "at least one of" a list of items refers to any combination of those items, including single members. As an example, "at least one of: a, b, or c" is intended to cover: a, b, c, a-b, a-c, b-c, and a-b-c.

As used herein, the term "or" is inclusive unless otherwise explicitly noted. Thus, the phrase "at least one of A, B, or C" is satisfied by any element from the set {A, B, C} or any combination thereof, including multiples of any element.

What is claimed is:

1. A system comprising:
an electrical line positioned in a wellbore proximate to one or more subsurface formations; and
a permanent downhole sensor array coupled to the electrical line and positioned, at least in part, within a cemented portion of the wellbore, the permanent downhole sensor array including one or more downhole sensors disposed inside set cement of the cemented portion of the wellbore, each downhole sensor including:
    a first spectral sensing device configured to detect at least a first component of a downhole fluid in the set cement.

2. The system of claim 1, further comprising:
a tubular positioned in the wellbore, wherein the wellbore is part of an injection well drilled through the one or more subsurface formations,
wherein the electrical line is coupled to the tubular,
wherein the tubular and the electrical line are cemented within the wellbore,
wherein the first spectral sensing device includes a first optical computational element configured to detect and quantify at least the first component of the downhole fluid within the wellbore for a lifetime of the injection well,
and wherein the downhole fluid is a pore fluid of the one or more subsurface formations.

3. The system of claim 1, further comprising:
a flow control device positioned proximate to a fractured zone of the wellbore and communicatively coupled to the first spectral sensing device, wherein the flow control device is configured to close upon detection of the first component by the first spectral sensing device.

4. The system of claim 1, further comprising:
a processor; and
a computer-readable medium having instructions executable by the processor, the instructions including:
    instructions to measure, via the permanent downhole sensor array, a quantity of the first component of the downhole fluid in one or more subsurface formations, wherein the permanent downhole sensor array is cemented in an injection well;
    instructions to update a reservoir model configured to model a travel of the first component through at least one of the subsurface formations; and
    instructions to alter an injection profile based, at least in part, on the updated reservoir model.

5. The system of claim 4, further comprising:
instructions to assess a health of the set cement in the wellbore based, at least in part, on the quantity of the first component; and
instructions to perform a wellbore operation to mitigate damage to the set cement in the wellbore.

6. The system of claim 1, wherein each downhole sensor of the permanent downhole sensor array includes an inlet filter configured to allow entry of the downhole fluid and inhibit cement flow into each respective spectral sensing device.

7. The system of claim 1, further comprising:
a three-phase flow meter communicatively coupled with the first spectral sensing device.

8. The system of claim 1, wherein the first spectral sensing device is configured to detect and to measure a quantity of at least a second component of the downhole fluid.

9. The system of claim 1, wherein each downhole sensor of the permanent downhole sensor array includes the first spectral sensing device and a second sensing device, wherein the second sensing device is configured to detect a presence and to measure a quantity of a second component of the downhole fluid.

10. An apparatus comprising:
a downhole sensor to be disposed inside set cement within a cemented portion of a wellbore proximate to one or more subsurface formations; and
a first spectral sensing device housed within the downhole sensor, the first spectral sensing device configured to identify at least a first component of a downhole fluid in the set cement.

11. The apparatus of claim 10, wherein the downhole sensor is configured to be cemented in a wellbore of an injection well drilled through the one or more subsurface formations, wherein the first spectral sensing device is configured to measure a quantity of the first component of the downhole fluid for a lifetime of the injection well, and wherein the downhole fluid is a pore fluid of the one or more subsurface formations.

12. The apparatus of claim 10, further comprising:
at least a second sensing device housed within the downhole sensor, wherein the second sensing device is configured to detect a second component of the downhole fluid.

13. The apparatus of claim 10, wherein the first spectral sensing device is configured to detect and to measure at least a second component of the downhole fluid.

14. The apparatus of claim 10, wherein the downhole sensor includes an inlet filter configured to allow entry of the downhole fluid and inhibit cement flow into the first spectral sensing device.

15. A method comprising:
positioning a permanent downhole sensor array including a first spectral sensing device within a wellbore formed in one or more subsurface formations, wherein the permanent downhole sensor array and the first spectral sensing device are to be embedded inside set cement within a cemented portion of the wellbore; and
configuring the first spectral sensing device to detect a first component of a downhole fluid inside the set cement.

16. The method of claim 15, further comprising:
injecting, via a wellbore of an injection well, the first component into the one or more subsurface formations;
updating a computerized reservoir model configured to model a travel of the first component through at least one of the subsurface formations based, at least in part, on the detecting of the first component; and
altering an injection profile of the injection well based, at least in part, on the updated computerized reservoir model,
wherein the permanent downhole sensor array is cemented in the wellbore of the injection well.

17. The method of claim 16, wherein altering the injection profile of the injection well based, at least in part, on the updated computerized reservoir model comprises altering the injection profile in real-time.

18. The method of claim 16, further comprising:
determining a quantity of the first component via at least the first spectral sensing device for a lifetime of the injection well.

19. The method of claim 15, further comprising:

assessing a health of the set cement in the wellbore based, at least in part, on the detection of the first component; and performing a wellbore operation to mitigate damage to the set cement in the wellbore.

20. The method of claim 16, further comprising:

injecting a second component into the one or more subsurface formations, wherein the second component travels through the one or more subsurface formations faster than the first component;

detecting the second component at a location of the permanent downhole sensor array;

updating the computerized reservoir model based on the detection of the second component; and predicting a travel path of the first component based on the detection of the second component.

* * * * *